(12) United States Patent
Nilsson et al.

(10) Patent No.: US 7,030,135 B2
(45) Date of Patent: Apr. 18, 2006

(54) INHIBITORS OF 11-β-HYDROXY STEROID DEHYDROGENASE TYPE 1

(75) Inventors: Marianne Nilsson, Rimbo (SE); Jerk Vallgårda, Uppsala (SE); Tjeerd Barf, Uppsala (SE)

(73) Assignee: Biovitrum AB, Stockholm (SE)

( * ) Notice: Subject to any disclaimer, the term of this patent is extended or adjusted under 35 U.S.C. 154(b) by 25 days.

(21) Appl. No.: 10/296,132

(22) PCT Filed: May 22, 2001

(86) PCT No.: PCT/SE01/01157

§ 371 (c)(1),
(2), (4) Date: Mar. 18, 2003

(87) PCT Pub. No.: WO01/90094

PCT Pub. Date: Nov. 29, 2001

(65) Prior Publication Data

US 2003/0199501 A1    Oct. 23, 2003

(30) Foreign Application Priority Data

May 22, 2000    (SE) .................................... 0001899

(51) Int. Cl.
*A61K 31/428*    (2006.01)
*C07D 277/82*    (2006.01)

(52) U.S. Cl. ...................... 514/301; 514/367; 546/114; 548/161

(58) Field of Classification Search ................. 548/161; 546/114; 514/301, 367
See application file for complete search history.

(56) References Cited

U.S. PATENT DOCUMENTS

| | | | |
|---|---|---|---|
| 2,362,087 | A | 11/1944 | Newbery |
| 4,254,260 | A | 3/1981 | Takaya et al. |
| 5,403,857 | A | 4/1995 | Edwards et al. |
| 5,594,021 | A | 1/1997 | Chan et al. |
| 5,783,597 | A | 7/1998 | Beers et al. |
| 5,856,347 | A | 1/1999 | Hashiguchi et al. |
| 5,962,490 | A | 10/1999 | Chan et al. |
| 6,030,991 | A | 2/2000 | Chan et al. |
| 2003/0130258 | A1 | 7/2003 | Kurz et al. |
| 2003/0130279 | A1 | 7/2003 | Jang et al. |
| 2003/0130318 | A1 | 7/2003 | Barf et al. |
| 2003/0166689 | A1 | 9/2003 | Kurz et al. |
| 2003/0176476 | A1 | 9/2003 | Barf et al. |

FOREIGN PATENT DOCUMENTS

| | | |
|---|---|---|
| EP | 0 749 964 A1 | 12/1996 |
| EP | 0 790 057 A1 | 8/1997 |
| EP | 0 819 681 A2 | 1/1998 |
| EP | 1 069 114 A2 | 1/2001 |
| FR | 94.123 | 5/1969 |
| FR | 2 384 498 A1 | 10/1978 |
| GB | 620654 | * 7/1940 |
| GB | 822 947 | 11/1959 |
| GB | 822947 | 11/1959 |
| GB | 6610324 | 1/1969 |
| JP | 2001483 A2 | * 1/1990 |
| JP | 03173876 A2 | 7/1991 |
| JP | 2001483 A | 3/1994 |
| NL | 6610324 | 1/1967 |
| WO | WO 96/04912 A1 | 2/1996 |
| WO | WO 97/07789 A1 | 3/1997 |
| WO | WO 98/16520 | 4/1998 |
| WO | WO 98/27081 | 6/1998 |
| WO | WO 98/36770 A1 | 8/1998 |
| WO | WO 99/02502 | 1/1999 |
| WO | WO 99/28306 A1 | 6/1999 |
| WO | WO 99/65884 | 12/1999 |
| WO | WO 00/02851 A1 | 1/2000 |
| WO | WO 01/01971 A1 | 1/2001 |

(Continued)

OTHER PUBLICATIONS

Huff, Journal of Medicinal Chemistry, vol. 34, No. 8, pp. 2305-2314, (1991).*

(Continued)

*Primary Examiner*—Joseph K. McKane
*Assistant Examiner*—Rebecce Anderson
(74) *Attorney, Agent, or Firm*—Foley & Lardner LLP

(57) ABSTRACT

The present invention relates to using a compound having the formula (I) wherein T is I) thienyl, which optionally is substituted with halogen, or II) phenyl optionally substituted with halogen and/or $C_{1-6}$-alkyl; E is a bond, —$CH_2$— or —CO—; L is a bond, —$CH_2$—, —$CHR^4$— or —$NR^3$—; $R^3$ is H, $C_{1-6}$-alkyl, $C_{1-6}$-acyl or —$COR^4$; $R^4$ is morpholino or $C_{1-6}$-amido; $R^6$ and $R^7$ are independently hydrogen or $C_{1-6}$-alkyl; and $R^8$ and $R^9$ are independently hydrogen or $C_{1-6}$-alkyl, as well as pharmaceutically acceptable salts, hydrates and solvates thereof, in the manufacture of a medicament for the treatment or prevention of diabetes, syndrome X, obesity, glaucoma, hyperlipidemia, hyperglycemia, hyperinsulinemia, osteoporosis, tuberculosis, dementia, depression, virus diseases and inflammatory disorders.

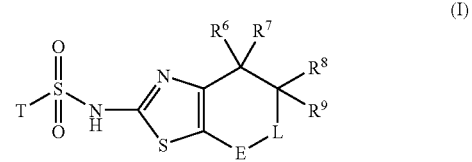

(I)

8 Claims, No Drawings

FOREIGN PATENT DOCUMENTS

| | | |
|---|---|---|
| WO | WO 01/52833 A1 | 7/2001 |
| WO | WO 01/54691 A1 | 8/2001 |
| WO | WO 01/90090 A1 | 11/2001 |
| WO | WO 01/90091 A1 | 11/2001 |
| WO | WO 02/28353 A2 | 4/2002 |
| WO | WO 03/011258 A1 | 2/2003 |

OTHER PUBLICATIONS

Hisamitsu Pharmaceutical Co: "Preparation of 2-(substituted amino)thiazole derivatives as esterase inhibitors," CAPLUS Accession No. 1995:818696, Document No. 123: 228174 (1995).

Hisamitsu Pharmaceutical Co: "Preparation of 2-aminothiazole derivatives as esterase inhibitors," CAPLUS Accession No. 1995:867676, Document No. 123:256699 (1995).

Susan Budavari et al., "The Merck Index, An Encyclopedia of Chemical, Drugs, and Biologicals, Twelfth Edition,", No. 9115, pp. 1529 (1996).

Friedrich Boberg et al., "Reaction of thioxo compounds with N-chloramidines. VI. Reaction of thioquinolone, dihydrothiazolethione and dihydroisothiazole thione with sodium N-chlorobenzenesulfonamides," CAPLUS Accession No. 1996:420288, Document No. 125:195596 (1996).

CHEMCATS Accession No. 1998:584450, Maybridge, Apr. 3, 2000, (1998).

CHEMCATS Accession No. 1998:584451, Maybridge, Apr. 3, 2000, (1998).

Hisamitsu Pharmaceutical Co: "Preparation of 2-(substituted amino)thiazole derivatives as esterase inhibitors," CAPLUS Accession No. 1995:818696, Document No. 123:228174 (1995).

Asahi Chemical Ind: "Therapeutics for Alzheimer's disease containing N-(5-nitro-2-thiazolyl)benzenesulfonamides," CAPLUS Accession No. 1996:111694, Document No. 124: 165271 (1996).

Hisamitsu Pharmaceutical Co: "Preparation of diphenylthiazoles as pharmaceuticals," CAPLUS Accession No. 1991: 680016, Document No. 115:280016, (1991).

Zaki El-Hewehi et al., "Sulfonic acid derivatives: preparation and applicability as mothproofing agents," Chemical Abstracts, vol. 58, The Abstract No. 5671, J. Prakt.Chem., pp. 297-336 (1962).

AsInEx Compound Collection, "5-Thiazolecarboxylic acid, 4-methyl-2-(((4-methylphenyl)sulfonyl)amino)-, ethyl ester, " CHEMCATS Accession No. 2001:67657, (2001).

Pharma Library Collection, "5-Thiazolecarboxylic acid, 2-(((4-chlorophenyl)sulfonyl)amino)-4-methyl-, ethyl ester," CHEMCATS Accession No. 2001:19109, (2001).

ChemDiv, Inc. Product Library, Apr. 26, 2001, "5-Thiazolecarboxylic acid, 4-methyl-2-(((4-methylphenyl) sulfonyl)amino-), ethyl ester," CHEMCATS Accession No. 2001:444469, (2001).

V.V. Berezhinskaya, "hypoglycemic activity in relation to chem. Structure of potential oral antidiabetic substances— (I) 1-sulfonyl-3-alkylureas, (II) analogs of 1-sulfonyl-3-alkylureas, (III) 2-benzene-sulfonamido-5-alkyl-1,3,4-thiadiazole and-oxadiazoles," CAOLD Accession No. CA57:3567g (1962).

Hans Wojahn, "Bromination of sulfapyrimidine and sulfathiazole compounds. II.," Chemical Abstracts, vol. 51, The Abstract No. 6646d, Arch. Pharm., pp. 288, 321-336 (1955).

V.A. Krasovskii et al., "Alkylation of aminothiazoles. VII. Alkylation of 2-aminothiazole and 4-methyl-2-aminothiazole by tert-butyl alcohol," CAPLUS Accession No. 1969:115051, Document No. 70: 115051, (1969).

J.D. McColl et al., "Effect of Some Sulfonylurea Derivatives in Experimental Ulcer Formation in the Rat," Chemical Abstracts, vol. 59, The Abstract No. 3231, Arch. Intern. Pharmacodyn, pp. 181-189 (1963).

Gaile E. Gudriniece et al., "Heterocyclic compounds based on diketones. II. 2'-Amino-5,5-dimethyl-1-cyclohexanone (2,3:4',5")thiazole. I.," Chemical Abstracts, vol. 59, The Abstract No. 6380 (1962).

Anton-Fos et al., "Pharmacological Studies of the Two New Hypoglycaemic Compounds 4-(3-Methyl-5-oxo-2-pyrazolin-1-yl)benzoic Acid and 1-(Mesitylen-2-sulfonyl)-1H-1,2,4-triazole," Arzneim.-Forsch./Drug Res 44(11), No. 7, 1994, pp. 821-826.

Merck & Co. Inc., USA, 1999, Monograph No. 4488, "Glybuzole," CAS Registry No. 1492-02-0.

Merck & Co. Inc., USA, 1999, Monograph No. 9084, "Sulfamethizole," CAS Registry No. 144-82-1.

CAPLUS, "2-Thiophenecarboxamide, N-2-naphthalenyl-3-((phenylsulfonyl)amino)-(9CI)", Caplus Registry No. 409362-65-8. (Supplement to Reference AS) (2002).

CAPLUS, "2-Thiophenecarboxamide, N-1-naphthalenyl-3-((phenylsulfonyl)amino)-(9CI)," Caplus Registry No. 409363-57-1. (Supplement to Reference AS) (2002).

CAPLUS, "2-Thiophenecarboxamide, 3-((phenylsulfonyl)amino)-N-(3-thienylmethyl)- (9CI)," Caplus Registry No. 409363-56-0. (Supplement to Reference AY) (1969).

CAPLUS, "2-Thiophenecarboxamide, 3-((phenylsulfonyl)amino)-N-(2-thienylmethyl)- (9CI),", Caplus Registry No. 409362-88-5. (Supplement to Reference AS) (2002).

CAPLUS, "2-Thiophenecarboxamide, N-(2-phenylethyl)-3-((phenylsulfonyl)amino)- (9CI),", Caplus Registry No. 409362-99-8. (Supplement to Reference AS) (2002).

CAPLUS, "2-Thiophenecarboxamide, N-(2,3-dimethylphenyl)-3-((phenylsulfonyl)amino)- (9CI)," Caplus Registry No. 409362-97-6. (Supplement to Reference AY) (1969).

CAPLUS, "2-Thiophenecarboxamide, N-(4-ethylphenyl)-3-((phenylsulfonyl)amino)- (9CI)," Caplus Registry No. 409362-93-2. (Supplement to Reference AS) (2002).

CAPLUS, "2-Thiophenecarboxamide, N-(2,6-dimethylphenyl)-3-((phenylsulfonyl)amino)- (9CI)," Caplus Registry No. 409362-72-7. (Supplement to Reference AS) (2002).

CAPLUS, "2-Thiophenecarboxamide, N-butyl-3-((phenylsulfonyl(amino)- (9CI)," Caplus Registry No. 409362-91-0. (Supplement to Reference AS) (2002).

CAPLUS, "2-Thiophenecarboxamide, N-(2-methoxyethyl)-3-((phenylsulfonyl)amino)- (9CI)," Caplus Registry No. 409363-48-0. (Supplement to Reference AS) (2002).

CAPLUS, "2-Thiophenecarboxamide, N-(2-methoxyethyl)-3-((phenylsulfonyl)amino)- (9CI)," Caplus Registry No. 409363-32-2. (Supplement to Reference AS) (2002).

CAPLUS, "2-Thiophenecarboxamide,N-(phenylmethyl)-3-((phenylsulfonyl)amino)- (9CI)," Caplus Registry No. 409362-89-6. (Supplement to Reference AS) (2002).

CAPLUS, "Benzenesulfonamide, 4-methoxy-N-(2-((1E)-2-(4-pyridinyl)ethenyl)-3-thienyl)- (9CI)," Caplus Registry No. 362629-53-6. (Supplement to Reference AS) (2002).

CAPLUS, "2-Thiophenecarboxamide, N-(1, 1-dimethylpropyl)-3-((phenylsulfonyl)amino)- (9CI)," Caplus Registry No. 409363-45-7. (Supplement to Reference AS) (2002).

CAPLUS, "2-Thiophenecarboxamide, N-(2-furanylmethyl)-3-((phenylsulfonyl)amino)- (9CI)," Caplus Registry No. 409363-44-6. (Supplement to Reference AS) (2002).

CAPLUS, "2-Thiophenecarboxamide, N-(4-(1-methylethyl) phenyl)-3-((phenylsulfonyl)amino)- (9CI)," Caplus Registry No. 409362-29-4. (Supplement to Reference AS) (2002).

Kim, C.H et al., J. Endocrinol, vol. 162, pp. 371-379 (1999).

C.G. Bellows et al., Bone, vol. 23, pp. 119-125 (1998).

M.S. Cooper et al., Bone, vol. 27, pp. 375-381 (2000).

Analgesic tetrahydrothiazolo[5, 4-c]pyridines, Fr. Addn., Addn to FR. 1498465, (1969).

Hökfelt, Bernt "Hypoglycemic Activity in Relation to Chemical Structure of Potential Oral Antidiabetic Substances. I. 1-Sulfonyl-3-alkylureas," *Journal of Medicinal and Pharmaceutical Chemistry*, 5(1):231-257 (Jan. 6, 1962) © American Chemical Society.

Sonino et al., "Ketoconazole treatment in Cushing's syndrome: experience in 34 patients," *Clinical Endocrinology* 35:347-352 (1991) © Blackwell Scientific Publications Ltd.

Verhelst et al., "Use of ketoconazole in the treatment of a virilizing adrenocortical carcinoma," *Acta Endocrinologica* 121:229-234 (1989) © Acta Endocrinologica (Copenhagen).

Beuchet, Eur. J. Med. Chem., 34(9), p. 773 (1999).

Desai et al., "Sulfonamides. II. Preparation of N1-hetrocyclic substituted sulfonamides from alpha-naphthylamine and evaluation of their antibacterial properties", J. Indian Chem. Soc. 46(2):115-118, (1969). CAPLUS accession No. 1969:412872, document No. 71:12872.

Desai et al., "Sulfonamides. IV. Some N-6-heterocyclic sulfonamides from 2-paphthylamine as possible antibacterial agents", J. Indian Chem. Soc. 46(2): 411-414, 1969. CAPLUS accession No. 1969:449825, document No. 71: 49825.

Gagiu et al., "Mitodepressive substances. 6.4-[(Haloacetyl) amino]-N1-$-benzenesulfonamides", Pharmazie 27(3):166, 1972. CAPLUS accession No. 1972:428762, document No. 77:28762.

DiCarlo et al., "Pentobarbital action on the binding capability of methylenoxytetracycline sulfaethylthiazole, and cyancobalamin with serum macromolecules", Atti Soc. Ital. Sci. Vet. 20:278-282, 1966, CAPLUS accession No. 1967: 4020611, document No. 67:2061.

Chaurasia et al., "Synthesis of some new 2-sulphanilamidothiazoles as potential fungicides", Agric. Biol. Chem. 45(5): 1129-1134, 1981. CAPLUS accession No. 1981-480840, document No. 95-80840.

Chemcats, "5-Thiazolecarboxylic acid, 4-methyl-2-(((4-methylphenyl)sulfonyl)amino)-, ethyl ester," Phrma Library Collection, (May 14, 2001). Chemcats Accession No. 2001: 20962, Order No. NS46076, CAS Registry No. 313230-18-1.

Chemcats, "5-Thiazolecarboxylic acid, 2-(((4-cholorophenyl) sulfonyl)amino)-4-methyl-, ethyl ester," Pharma Library Collection, (May 14, 2001). Chemicals Accession No. 2001:19109, Order No. NS41693, CAS Registry No. 312915-26-7.

Chemcats, "5-Thiazolecarboxylic acid, 4-methyl-2-(((3-nitrophenyl)sulfonyl)amino)-, ethyl ester," ChemDiv. Inc. Product Library, (Apr. 26, 2001). Chemcats Accession No. 2001:786400, Order No. 0947-0103. CAS Registry No. 313237-92-2.

Chemcats, "5-Thiazolecarboxylic acid, 4-methyl-2-((phenylsulfonyl)amino)-, ethyl ester," Pharma Library Collection, (May 14, 2001). Chemcats Accession No. 2001: 2446055, Order No. NS44365, CAS Registry No. 313237-91-1.

Chemcats, "5-Thiazolecarboxylic acid, 4-methyl-2-((2-naphthalenylsulfonyl)amino)-, ethyl ester," Pharma Library Collection, (May 14, 2001). Chemcats Accession No. 2001: 19110, Order No. NS41694, CAS Registry No. 312915-27-8.

Chemcats, "5-Thiazolecarboxylic acid, 4-methyl-2-((4-methylphenyl)sulfonyl)amino)-, ethyl ester," Compounds for Screening, (Jul. 1, 2001). Chemcats Accession No. 2001:1499370, Order No. AG-690/36005052. CAS Registry No. 313230-18-1.

Chemcats, "5-Thiazolecarboxylic acid, 2-(((2-chlorophenyl) sulfonyl)amino)-4-methyl-ethyl ester," Interbioscreen Compound Library, (Feb. 11, 2002). Chemcats Accession No. 2002:175108, Order No. STOCK2S-28380, CAS Registry No. 378764-18-2.

Chemcats, "5-Thiazolecarboxamide, 4-methyl-N-phenyl-2-((phenylsulfonyl)amino)-," Interbioscreen Compound Library, (Feb. 11, 2002). Chemcats Accession No. 2002: 174900, Order No. STOCK2S-27987, CAS Registry No. 378768-75-3.

Chemcats, "5-Thiazolecarboxamide, 2-(((2,5-dimethylphenyl)sulfonyl)amino)-4-methyl-N-phenyl-," Interbioscreen Compound Library, (Feb. 11, 2002). Chemcats Accession No. 2002:310940, Order No. STOCK2S-37273, CAS Registry No. 380584-86-1.

Chemcats, "5-Thiazolecarboxamide, 4-methyl-2-(((4-methylphenyl)sulvonyl)amino)-N-phenyl-," Interbioscreen Compound Library, (Feb. 11, 2002). Chemcats Accession No. 2002:310143, Order No. STOCK2S-35716, CAS Registry No. 380590-91-0.

Chemcats, "5-Thiazolecarboxylic acid, 2-(((2,5-dimethylphenyl)sulfonyl)amino)-4-methyl-, ethyl ester," Interbioscreen Compound Library, (Feb. 11, 2002). Chemcats Accession No. 2002:312516, Order No. STOCK2S-40385, CAS Registry No. 380878-60-4.

* cited by examiner

INHIBITORS OF 11-β-HYDROXY STEROID DEHYDROGENASE TYPE 1

CROSS REFERENCE TO RELATED APPLICATIONS

The present application is a national phase application under 35 U.S.C. Section 371 filed from International Patent Application PCT/SE01/01157, filed 22 May 2001, which claims priority to Swedish patent application Serial. No. 0001899-4, filed 22 May 2000. The contents of these applications are incorporated herein by reference in their entirety.

TECHNICAL FIELD

The present invention relates to novel compounds, to pharmaceutical compositions comprising the compounds, to processes for their preparation, as well as to the use of the compounds in medicine and for the preparation of a medicament which acts on the human 11-β-hydroxysteroid dehydrogenase type 1 enzyme (11βHSD1).

BACKGROUND ART

1. Glucorticoids, Diabetes and Hepatic Glucose Production

It has been known for more than half a century that glucocorticoids have a central role in diabetes, e.g. the removal of the pituitary or the adrenal gland from a diabetic animal alleviates the most severe symptoms of diabetes and lowers the concentration of glucose in the blood (Long, C. D. and F. D. W. Leunins (1936) J. Exp. Med. 63: 465–490; Houssay, B. A. (1942) Endocrinology 30: 884–892). It is also well established that glucocorticoids enable the effect of glucagon on the liver.

The role of 11βHSD1 as an important regulator of local glucocorticoids effect and thus of hepatic glucose production is well substantiated (see e.g. Jamieson et al. (2000) J. Endocrinol. 165: p. 685–692). The hepatic insulin sensitivity was improved in healthy human volunteers treated with the non-specific 11βHSD1 inhibitor carbenoxolone (Walker, B. R et al. (1995) J. Clin. Endocrinol. Metab. 80: 3155–3159). Furthermore, the expected mechanism has been established by different experiments with mice and rats. These studies showed that the MRNA levels and activities of two key enzymes in hepatic glucose production were reduced, namely: the rate-limiting enzyme in gluconeogenesis, phosphoenolpyrnvate carboxykinase (PEPCK), and glucose-6-phosphatase (G6Pase) catalyzing the last common step of gluconeogenesis and glycogenolysis. Finally, the blood glucose level and hepatic glucose production is reduced in mice having the 11βHSD1 gene knocked-out. Data from this model also confirm that inhibition of 11βHSD1 will not cause hypoglycemia, as predicted since the basal levels of PEPCK and G6Pase are regulated independently of glucocorticoids (Kotelevtsev, Y. et al., (1997) Proc. Natl. Acad. Sci. USA 94: 14924–14929).

2. Possible Reduction of Obesity and Obesity Related Cardiovascular Risk Factors Obesity is an important factor in syndrome X as well as in the majority (>80%) of type 2 diabetic, and omental fat appears to be of central importance. Abdominal obesity is closely associated with glucose intolerance, hyperinsulinemia, hypertiglycefidemia, and other factors of the so-called syndrome X (e.g. raised blood pressure, decreased levels of HDL and increased levels of VLDL) (Montague & O'Rahilly, Diabetes 49: 883–888, 2000). Ihiibition of the enzyme in pre-adipocytes (stromal cells) has been shown to decrease the rate of differentiation into adipocytes. This is predicted to result in dimniliished expansion (possibly reduction) of the omental fat depot, i.e. reduced central obesity (Bujalska, I. J., S. Kumar, and P. M. Stewart (1997) Lancet 349: 1210–1213).

Inhibition of 11βHSD1 in mature adipocytes is expected to attenuate secretion of the plasminogen activator inhibitor 1 (PAI-1)—an independent cardiovascular risk factor (Halleux, C. M. et al. (1999) J. Clin. Endocrinol. Metab. 84: 4097–4105). Furthermore, there is a clear correlation between glucocorticoid "activity" and cardiovascular risk factor suggesting that a reduction of the glucocorticoid effects would be beneficial (Walker, B. R et al. (1998) Hypertension 31: 891–895; Fraser, R. et al. (1999) Hypertension 33: 1364–1368).

Adrenalectomy attenuates the effect of fasting to increase both food intake and hypothalamic neuropeptide Y expression. This supports the role of glucocorticoids in promoting food intake and suggests that inhibition of 11βHSD1 in the brain might increase satiety and therefore reduce food intake (Woods, S. C. et al. (1998) Science, 280: 1378–1383).

3. Possible Beneficial Effect on the Pancreas

Inhibition of 11βHSD1 in isolated urine pancreatic 13-cells improves the glucose-stimulated insulin secretion (Davani, B. et al. (2000) J. Biol. Chem. 2000 Nov. 10, 275(45):34841–4). Glucocorticoids were previously known to reduce pancreatic insulin release in vivo (illaudel, B. and B. C. J. Sutter (1979) Horm. Metab. Res. 11: 555–560). Thus, inhibition of 11βHSD1 is predicted to yield other beneficial effects for diabetes treatment, besides effects on liver and fat.

4. Possible Beneficial Effects on Cognition and Dementia

Stress and glucocorticoids influence cognitive function (de Quervain, D. J.-F., B. Roozendaal, and J. L. McGaugh (1998) Nature 394: 787–790). The enzyme 11βHSD1 controls the level of glucocorticoid action in the brain and thus contributes to neurotoxicity (Rajan, V., C. R. W. Edwards, and J. R Secki, J. (1996) Neuroscience 16: 65–70; Seckl, J. R., Front. (2000) Neuroendocrinol. 18: 49–99). Unpublished results indicate significant memory improvement in rats treated with a non-specific 11βHSD1 inhibitor (J. Seckl, personal communication). Based the above and on the known effects of glucocorticoids in the brain, it may also be suggested that inhibiting 11βHSD1 in the brain may result in reduced arriety (Tronche, F. et al. (1999) Nature Genetics 23: 99–103). Thus, taken together, the hypothesis is that inhibition of 11βHSD1 in the human brain would prevent reactivation of cortisone into cortisol and protect against deleterious glucocorticoid-mediated effects on neuronal survival and other aspects of neuronal function, including cognitive impairment, depression, and increased appetite (previous section).

5. Possible Use of Immuno-Modulation Using 11βHSD1 Inhibitors

The general perception is that glucocorticoids suppress the immune system. But in fact there is a dynamic interaction between the immune system and the HPA hypothalamo-pitaitary-adrenal) axis (Rook, G. A. W. (1999) Baillièr's Clin. Endocrinol. Metab. 13: 576–581). The balance between the cell-mediated response and humoral responses is modulated by glucocorticoids. A high glucocorticoid activity, such as at a state of stress, is associated with a humoral response. Thus, inhibition of the enzyme 11βHSD1 has been suggested as a means of shifting the response towards a cell-based reaction.

In certain disease states, including tuberculosis, lepra and psoriasis the immune reaction is normally biased towards a humoral response when in fact the appropriate response would be cell based. Temporal inhibition of 11βHSD1, local or systemic, might be used to push the immune system into the appropriate response (Mason, D. (1991) Immunology Today 12: 57–60; Rook et al., supra).

An analogous use of 11βHSD1 inhibition, in this case temporal would be to booster the immune response in association with immunization to ensure that a cell based response would be obtained, when desired.

6. Reduction of Intraocular Pressure

Recent data suggest that the levels of the glucocorticoid target receptors and the 11βHSD enzymes determines the susceptibility to glaucoma (Stokes, J. et al. (2000) Invest. Ophthalmol. 41: 1629–1638). Further, inhibition of 11βHSD1 was recently presented as a novel approach to lower the intraocular pressure (Walker E. A. et al, poster P3-698 at the Endocrine society meeting Jun. 12–15, 1999, San Diego). Ingestion of carbenoxolone, a non-specific inhibitor of 11βHSD1, was shown to reduce the intraocular pressure by 20% in normal subjects. In the eye, expression of 11βHSD1 is confined to basal cells of the corneal epithelium and the non-pigmented epithelialium of the cornea (the site of aqueous production), to culinary muscle and to the sphincter and dilator muscles of the iris. In contrast, the distant isoenzyme 11βHSD2 is highly expressed in the non-pigmented ciliary epithelinm and corneal endothelium. None of the enzymes is found at the trabecular meshwork, the site of drainage. Thus, 11βHSD1 is suggested to have a role in aqueous production, rather than drainage, but it is presently unknown if this is by interfering with activation of the glucocorticoid or the mineralocorticoid receptor, or both.

7. Reduced Osteoporosis

Glucocorticoids have an essential role in skeletal development and function but are detrimental in excess. Glucocorticoid-induced bone loss is derived, at least in part via inhibition of bone formation, which includes suppression of osteoblast proliferation and collagen synthesis (Kim, C. H., S. L. Cheng, and G. S. Kim (1999) J. Endocrinol. 162: 371–379). The negative effect on bone nodule formation could be blocked by the non-specific inhibitor carbenoxolone suggesting an important role of 11βHSD1 in the glucocorticoid effect (Bellows, C. G., A. Ciaccia, and J. N. M. Heersche, (1998) Bone 23: 119–125). Other data suggest a role of 11βHSD1 in providing sufficiently high levels of active glucocorticoid in osteoclasts, and thus in augmenting bone resorption (Cooper, M. S. et al. (2000) Bone 27: 375–381). Taken together, these different data suggest that inhibition of 11βHSD1 may have beneficial effects against osteoporosis by more than one mechanism working in parallel.

WO 99/65884 discloses carbon substituted aminothiazole inhibitors of cyci dependent kinases. These compounds may e.g. be used against cancer, inflammation and arthritis. U.S. Pat. No. 5,856,347 discloses an antibacterial preparation or bactericide comprising 2-aminothiazole derivative and/or salt thereof. Further, U.S. Pat. No. 5,403,857 discloses benzenesulfonamide derivatives having 5-lipoxygenase inhibitory activity. Additionally, tetrahydrothiazolo[5,4-c] pyridines are disclosed in: Analgesic tetrahydrothiazolo[5, 4-c]pyridines. Fr. Addn. (1969), 18 pp, Addn. to Fr. 1498465. CODEN: FAXXA3; FR 94123 19690704 CAN 72:100685 AN 1970: 100685 CAPLUS and 4,5,6,7-Tetrahydrothiazolo[5,4-c]pyridines. Neth. Appl. (1967), 39 pp. CODEN:NAXXAN NL 6610324 19670124 CAN 68: 49593, AN 1968: 49593 CAPLUS.

FR 2384498 discloses thiazolo-benzenesulfonamides which show antibacterial antifungal and hypoglycaemic properties. WO99/28306 and EP 0 819 681 A2 relate to thiazolobenzenesulfonamides which can be used for treating neurodegenerative pathologies, such as Alzheimer's disease. JP 7149745 A2 and JP 7149746 A2 both describe 2-aminothiazole derivatives as esterase inhibitors. Nothing is disclosed about inhibiting 11βHSD1. JP 7309757 A2 relates to treating Alzheimer's disease using N-(5-nitro-2-thiazolyl) benzenesulfonamides. JP 3173876 A2 presents preparation of diphenylthiazoles. These compounds are used as anti-inflammatores, analgesics, anti-allergy agents, uric acid accelerators and blood platelet aggregation inhibitors. EP 0 790 057 A1 discloses an antibacterial or bactericide comprising a 2-aminothiazole derivative. U.S. Pat. No. 2,362, 087 describes the preparation of thiazolobenzenesulfonamides, such as 2-bromobenzenesulfonamido4-methylthiazole. Nothing is disclosed about inhibiting 11βHSD1 and no therapeutic use of such substances is disclosed.

However, none of the above disclosures discloses the compounds according to the present invention, or their use for the treatment of diabetes, obesity, glaucoma, osteoporosis, cognitive disorders, immune disorders, and depression.

Consequently, there is a need of new compounds that are useful in the treatment of diabetes, obesity, glaucoma, osteoporosis, cognitive disorders, immune disorders, and depression.

DISCLOSURE OF THE INVENTION

The compounds according to the present invention solve the above problems and embraces a novel class of compounds which has been developed and which inhibit the human 11-β-hydroxysteroid dehydrogenase type 1 enyme (11-β-$HSD_1$), and may therefore be of use in the treating disorders such as diabetes, obesity, glaucoma, osteoporosis, cognitive disorders; immune disorders, and depression.

One object of the present invention is compound of formula (I)

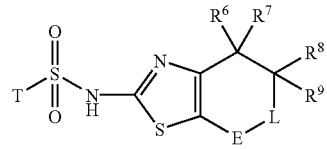

wherein
T is
I) thienyl which optionally is substituted with at least one halogen, or
II phenyl substituted with
a) at least one $C_{2-6}$-alkyl; or
b) at least one $C_{1-6}$-alkyl and at least one halogen; or
c) at least three halogens;
E is a bond, —$CH_2$— or —CO—;
L is a bond, —$CH_2$—, —$CHR^4$— or —$NR^3$—;
$R^3$ is H, $C_{1-6}$-alkyl $C_{1-6}$-acyl or —$COR^4$;
$R^4$ is morpholinyl or $C_{1-6}$ amido;
$R^6$ and $R^7$ are independently hydrogen or $C_{1-6}$-alkyl; and $R^8$ and $R^9$ are independently hydrogen or $C_{1-6}$-alkyl as well as pharmaceutically acceptable salts, hydrates and solvates thereof It is preferred that:

T is

I) thienyl, which is substituted with at least one halogen selected from chloro and bromo, or II) phenyl substituted with a) at least one n-propyl; or b) at least one methyl and at least one halogen selected from chloro and bromo; or c) at least three halogens selected from fluoro, bromo and chloro;

E is a bond, —CH$_2$— or —CO—;

L is a bond, —CH$_2$—, —CHR$^4$— or —NR$^3$—;

R$^3$ is methyl, acetyl or —COR$^4$;

R$^4$ is morpholinyl or propionamido;

R$^6$ and R$^7$ are both hydrogen; and

R$^8$ and R$^9$ are independently hydrogen or methyl.

Specific examples of compounds according to the present invention are:

N-(5-Acetyl-4,5,6,7-tetrahydro[1,3]thiazolo[5,4c]pyridin-2-yl)-3-chloro-2-methylbenzenesulfonamide;

2,4-dichloro-6-methyl-N-(5,6,6-trimethyl4,5,6,7-tetrahydro [1,3]thiazolo[5,4-c]pyridin-2-yl)benzenesulfonamide;

2,4-dichloro-6-methyl-N-[5-(4-morpholinylcarbonyl)-4,5,6, 7-tetrahydro[1,3]thiazolo[5,4-c]pyridin-2-yl]benzenesulfonamide;

2,4-Dichloro-6-methyl-N-(4,5,6,7-tetrahydro-1,3-benzothiazol-2-yl)benzenesulfonamide;

4Bromo-N-(5,6-dihydro-4H-cyclopenta[d][1,3]thiazol-2-yl)-2,5-difluorobenzenesulfonamide;

2,3,4-Trichloro-N-(5,6-dihydro-4H-cyclopenta[d][1,3]thiazol-2-yl)benzenesulfonamide;

N-(2-{[(2,4-dichloro-6methylphenyl)sulfonyl]amino}-4,5, 6,7-tetrahydro-1,3-benzothiazol-6-yl)propanamide;

2,4-Dichloro-N-(5,5-dimethyl-7-oxo-4,5,6,7-tetrahydro-1, 3-benzothiazol-2-yl)-6-methylbenzenesulfonamide;

2,3,4-Trichloro-N-(5,5-dimethyl-7-oxo-4,5,6,7-tetrahydro-1,3-benzothiazol-2-yl)benzenesulfonamide;

4,5-Dichloro-N-(5,5-dimethyl-7-oxo-4,5,6,7-tetrahydro-1, 3-benzothiazol-2-yl)-2-thiophenesulfonaemide;

4-Bromo-5-chloro-N-(5,5-dimethyl-7-oxo-4,5,6,7-tetrahydro-1,3-benzothiazol-2-yl)-2-thiophenesulfonamide;

3-Bromo-5-chloro-N-(5,5-dimethyl-7-oxo-4,5,6,7-tetrahydro-1,3-benzothiazo1-2-yl)-2-thiophenesulfonamide;

N-(5-Methyl-7-oxo-4,5,6,7-tetrahydro-1,3-benzothiazol-2-yl)4-propylbenzenesulfonamide;

4,5-Dichloro-N-(5-methyl-7-oxo-4,5,6,7-tetrahydro-1,3-benzothazol-2-yl)-2-thiophenesulfonamide;

2,4-Dichloro-6-methyl-N-(5-methyl-7-oxo-4,5,6,7-tetrahydro-1,3-benzothiazol-2-yl)benzenesulfonamide; and 4-Bromo-2-methyl-N-(5-methyl-7-oxo-4,5,6,7-tetrahydro-1,3-benzothiazol-2-yl)benzenesulfonamide.

Another object of the present invention is compound as described above for medical use.

The compounds as described above can be prepared by methods comprising at least one of the following steps:

a) sulfonamide coupling by reacting a 2-aminothiazole with a sulfonylcbloride in the presence of abase, b) sulfonamide coupling by reacting a 2-aminothiazole derivative with a sulfonylchloride in the presence of a base.

Another object of the present invention is a method for the treatment or prevention of diabetes, syndrome X obesity, glaucoma, hyperlipidemia, hyperglycemia, hyperinsulinemia, osteoporosis, tuberculosis, dementia, depression, virus diseases and inflammatory disorders, said method comprising administering to- a mammal, including man, in need of such treatment, an effective amount of a compound having the formula (I)

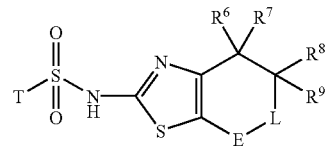

wherein

T is

I) thienyl which optionally is substituted with halogen, or

II) phenyl optionally substituted with halogen and/or $C_{1-6}$-alkyl;

E is a bond, —CH$_2$— or —CO—;

L is a bond, —CH$_2$—, —CHR$^4$— or —NR$^3$—;

R$^3$ is H, $C_{1-6}$-alkyl, $C_{1-6}$-acyl or —COR$^4$;

R$^4$ is morpholino or $C_{1-6}$-amido;

R$^6$ and R$^7$ are independently hydrogen or $C_{1-6}$-alkyl; and

R$^8$ and R$^9$ are independently hydrogen or $C_{1-6}$-alkyl, as well as pharmaceutically acceptable salts, hydrates and solvates thereof.

These compounds may also be used in the manufacture of a medicament for the treatment or prevention of diabetes, syndrome X obesity, glaucoma, hyperlipidemia, hyperglycemia, hyperinsulinemia, osteoporosis, tuberculosis, dementia, depression, virus diseases and inflammatory disorders.

It is preferred that:

T is

I) thienyl which is substituted with at least one halogen selected from chloro and bromo, or II) phenyl, which is substituted with at least one of methyl n-propyl, fluoro, chloro and bromo;

E is a bond, —CH$_2$— or —CO—;

L is a bond, —CH$_2$—, —CHR$^4$— or —NR$^3$—;

R$^3$ is methyl acetyl or —COR$^4$;

R$^4$ is morpholinyl or propionamido;

R$^6$ and R$^7$ are both hydrogen; and

R$^8$ and R$^9$ are independently hydrogen or methyl.

Specific examples of compounds according to the present invention are given above.

Another object of the present invention is a pharmaceutical composition comprising at least one compound of the formula (I) as defined above, and a pharmaceutically acceptable carrier.

The compounds according to the present invention may be used in several indications which involve 11-β-hydroxysteroid dehydrogenase type 1 enzyme. Thus the compounds according to the present invention may be used against dementia (see WO97/07789), osteoporosis (see Canalis E 1996, Mechanisms of glucocorticoid action in bone: implications to glucocorticoid-induced osteoporosis, Journal of Clinical Endocrinology and Metabolism, 81, 3441–3447) and may also be used disorders in the immune system (see Franchimont et al, "Inhibition of Th1 immune response by glucocorticoids: dexamethasone selectively inhibits IL-12-induced Stat 4 phosphorylation in T lymphocytes", The journal of Immunology 2000 Feb. 15, vol. 164 (4), pages 1768–74) and also in the above listed indications.

The various terms used, separately and in combinations, in the above definition of the compounds having the formula (I) will be explained.

The term "aryl" in the present description is intended to include aromatic rings (monocyclic or bicyclic) having from 6 to 10 ring carbon atoms, such as phenyl (Ph) and naphthyl, which optionally may be substituted by $C_{1-6}$-alkyl. Examples of substituted aryl groups are bezyl, and 2-methylphenyl.

The term "heteroaryl" means in the present description a monocyclic, bi- or tricyclic aromatic ring system (only one ring need to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen and selenium Examples of such heteroaryl rings are pyrrole, imidazole, thiophene, A, thiazole, isothiazole, thiadiazole, oxazole, isoxazole, oxadiazole, pyridine, pyrazine, pyrimidine, pyridazine, pyrazole, tiazole, tetrazole, chroman, isochroman, qunolininoqulinoxaline, isoquinoline, phthalazine, cinnoline, quinazoline, indole, isoindole, indoline, isoindoline, benzothiophene, benzofurau, isobenzofuran, benzoxazole, 2,1,3-benzoxadiazole, benzothiazole, 2,1,3-benzothiazole, 2,1,3-benzoselenadiazole, benzimidazole, indazole, benzodioxane, indane, 1,2,3,4-tetrahydroquinoline, 3,4-dihydro-2H-1,4-benzoxazine, 1,5-naphthyridine, 1,8-naphthyridine, acridine, fenazine and xanthene.

The term "heterocyclic" in the present description is intended to include unsaturated as well as partially and fully saturated mono-, bi- and tricyclic rings having from 4 to 14, preferably 4 to 10 ring atoms, such as, for example, the heteroaryl groups mentioned above as well as the corresponding partially saturated or fully saturated heterocyclic rings. Exemplary saturated heterocyclic rings are azefidine, pyrrolidine, piperidine, piperazine, morpholine, thiomorpholine and 1,4-oxazepane.

$C_{1-6}$-alkyl in the compound of formula (I) according to the present application, which may be straight, branched or cyclic, is preferably $C_{1-4}$-allyl. Exemplary alkyl groups include methyl, ethyl, n-propyl isopropyl n-butyl, sec-butyl tert-butyl, pentyl isopentyl, hexyl isohexyl and cyclohexyl.

$C_{2-6}$-alkyl in the compound of formula (I) according to the present application, which may be straight, branched or cyclic, is preferably $C_{2-4}$-alkyl. Exemplary alkyl groups include ethyl, u-propyl, isopropyl n-butyl sec-butyl, tert-butyl pentyl, isopentyl, hexyl isohexyl, and cyclohexyl.

$C_{1-6}$-acyl, in the compound of formula (I) according to the present application may be saturated or unsaturated and is preferably $C_{1-4}$-acyl. Exemplary acyl groups include formyl, acetyl propionyl butyryl, isobutyryl, valeryl isovaleryl, butenoyl (e.g. 3-butenoyl), hexenoyl (e.g. 5-hexenoyl).

$C_{1-6}$-amido, in the compound of formula (I) according to the present application may be saturated or unsaturated and is preferably $C_{1-4}$-amido. Exemplary amido groups include formamido, acetamido, propionamido, butyramido, isobutyramido, valeramido, isovaleramido, butenamido (e.g. 3-butenamido), hexenamido (e.g. 5-hexenamido).

The term "halogen" in the present description is intended to include fluorine, chlorine, bromine and iodine.

With the expression mono- or di-substituted is meant in the present description that the functionalities in question may be substituted with independently H, $C_{1-6}$-acyl, $C_{1-6}$-alkenyl, $C_{1-6}$-(cyclo)allcyl, aryl pyridylmethyl, or heterocyclic rings e.g. azetidine, pyrrolidine, piperidine, piperazine, morpholine and thiomorpholine, which heterocyclic rings optionally may be substituted with $C_{1-6}$-alkyl.

The term "prodrug forms" in the present description means a pharmacologically acceptable derivative, such as an ester or an amide, which derivative is biotransformed in the body to form the active drug (see Goodman and Gilman's, The Pharmacological basis of Therapeutics, 8$^{th}$ ed., McGraw-Hill, Int. Ed. 1992, "Biotransformation of Drugs, p. 13–15).

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean in the present description salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, truoroacetic acid, finmaric acid, succinic acid, tartic acid, citric acid, benzoic acid, ascorbic acid and the like. Base addition salts may be formed with organic and inorganic bases, such as sodium, ammonia, potassium calcium, ethanolamine, diethanolamine, N-methylglucamine, choline and the like.

Pharmaceutical compositions according to the present invention contain a pharmaceutically acceptable carrier together with at least one of the compounds comprising the formula (I) as described herein above, dissolved or dispersed therein as an active, antimicrobial, ingredient. In a preferred embodiment, the therapeutic composition is not immunogenic when administered to a human patient for therapeutic purposes, unless that purpose is to induce an imune response.

The preparation of a pharmacological composition that contains active ingredients dissolved or dispersed therein is well understood in the art Typically such compositions are prepared as sterile injectables either as liquid solutions or suspensions, aqueous or non-aqueous, however, solid forms suitable for solution, or suspensions, in liquid prior to use can also be prepared The preparation can also be emulsified.

The active ingredient may be mixed with excipients, which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition may contain minor amounts of vary substances such as wetting or emulsifying agents, pH buffering agents and the like which enhance the effectiveness of the active ingredient. Adjuvants may also be present in the composition.

Pharmaceutically acceptable carriers are well known in the art Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerine, vegetable oils such as cottonseed oil, organic esters such as ethyl oleate, and water-oil emulsions.

The pharmaceutical composition according to one of the preferred embodiments of the present invention comprising compounds comprising the formula (I), may include pharmaceutically acceptable salts of that component therein as set out above. Pharmaceutically acceptable salts include the acid addition salts (formed with the free amino groups of the polypeptide) that are formed with inorganic acids such as, for example, hydrochloric or phosphoric acids, or such organic acids as acetic acid, tartaric acid, mandelic acid and the like. Salts formed with the free carboxyl groups can also be derived from inorganic bases such as, for example, sodium, potassium, ammonium, calcium or ferric hydroxides, and such organic bases as isopropylamine, timethylamine, 2-ethylamino ethanol, histidine, procaine and the like.

The preparations according to the preferred embodiments may be administered orally, topically, intraperitoneally, intraarticularly, intracranially, intradermally, intramuscularly, intraocularly, intrathecally, intravenously, subcutaneously. Other routes which are known for the skilled person in the art are thinkable.

The orally administrable compositions according to the present invention may be in the form of tablets, capsules, powders, granules, lozenges, liquid or gel preparations, such as oral, topical or sterile parenteral solutions or suspensions. Tablets and capsules for oral administration may be in unit dose presentation form and may contain conventional excipients such as binding agents, for example syrup, acacia, gelatin, sorbitol, traganath or polyvinyl-pyrrolidone; fillers e.g. lactose, sugar, maize-starch, calcium phosphate, sorbitol or glycine; tabletting lubricant e.g. magnesium stearate, talc, polyethylene glycol or silica; disintegrants e.g. potato starch, or acceptable wetting agents such as sodium lauryl sulfate. The tablets may be coated according to methods well known in normal pharmaceutical practice. Oral liquid preparations may be in the form of e.g. aqueous or oily suspensions, solutions, emulsions, syrups or elixirs or may be presented as a dry product for reconstitution with water or other suitable vehicle before use. Such liquid preparations may contain conventional additives such as suspending agents, e.g. sorbitol, syrup, methyl cellulose, glucose syrup, gelatin hydrogenated edible fats; emulsffying agents e.g. lecithin, sorbitol monooleate or acacia, non-aqueous vehicles (which may include edible oils), e.g. almond oil, fractionated coconut oil, oily esters such as glycerine, propylene glycol or ethyl alcohol; preservatives e.g. methyl or propyl p-hydroxybenzoate or sorbic acid, and if desired conventional flavouring or colouring agents.

A pharmaceutical composition according to the present invention, may comprise typically an amount of at least 0.1 weight percent of compound comprising the formula (I) per weight of total therapeutic composition. A weight percent is a ratio by weight of total composition. Thus, for example, 0.1 weight percent is 0.1 grams of compound comprising the formula (I) per 100 grams of total composition. A suitable daily oral dose for a mammal preferably a human being, may vary widely depending on the condition of the patient. However a dose of compound comprising the formula (I) of about 0.1 to 300 mg/kg body weight may be appropriate.

The compositions according to the present invention may also be used veterinarily and thus they may comprise a veterinarily acceptable excipient or carrier.

The compounds of the present invention in labelled form, e.g. isotopically labelled, may be used as a diagnostic agent.

The compounds of the formula (I) above may be prepared by, or in analogy with, conventional methods, and especially according to or in analogy with the following methods. Further, the pharmacology in-vitro was studied using the following reagents and methods.

All publications mentioned herein are hereby incorporated by reference. By the expression "comprising" we understand including but not limited to. Thus, other non-mentioned substances, additives or carriers may be present.

The invention will now be described in reference to the following Figures and Examples. These Figures and Examples are not to be regarded as limiting the scope of the present invention, but shall only serve in an illustrative manner.

Experimental Methods

Scintillation Proximity Assay

[1,2(n)-$^3$H]-cortisone was purchased from Amersham Pharmacia Biotech. Anti-cortisol monoclonal mouse antibody, clone 6D6.7 was obtained from Immunotech and Scintillation proximity assay (SPA) beads coated with monoclonal antimouse antibodies were from Amersham Pharmacia Biotech. NADPH, tetrasodium salt was from Calbiochem and glucose-6-phosphate (G-6-P) was supplied by Sigma The human 11-β-hydroxysteroid dehydrogenase type-1 enzyme (11-β-HSD$_1$) was expressed in *Pichia pastoris*. 18-β-glycyrhetinic acid (GA) was obtained from Sigma. The serial dilutions of the compounds were performed on a Tecan Genesis RSP 150. Compounds to be tested were dissolved in DMSO (1 mM) and diluted in 50 mM Tri-HCl, pH 7.2 containing 1 mM EDTA The multiplication of plates was done on a WallacQuadra. The amount of the product [$^3$H]-cortisol, bound to the beads was determined in a Packard, Top Count microplate liquid scintillation counter.

The 11-β-HSD$_1$ enzyme assay was carried out in 96 well microtiter plates (Packard, Optiplate) in a total well volume of 220 µL and contained 30 mM Tris-HCl pH 7.2 with 1 mM EDTA, a substrate mixture tritiated Cortisone/NADPH (175 nM/181 µM, G-6-P (1 mM) and inhibitors in serial dilutions (9 to 0.15 µM. Reactions were initiated by the addition of human 11-β-HSD$_1$, either as *Pichia pastoris* cell homogenate or microsomes prepared from *Pichia pastoris* (the final amount of enzyme used was varied between 0.057 to 0.11 mg/mL). Following mixing, the plates were shaken for 30 to 45 minutes at room temperature. The reactions were terminated with 10 µL 1 mM GA stop solution. Monoclonal mouse antibody was then added (10 µL of 4 µM) followed by 100 µL of SPA beads (suspended according to the manufacturers instructions). Appropriate controls were set up by omitting the 11-β-HSD$_1$ to obtain the non-specific binding (NSB) value.

The plates were covered with plastic film and incubated on a shaker for 30 minutes, at room temperature, before counting. The amount of [$^3$H]-cortisol, bound to the beads was determined in a microplate liquid scintillation counter.

The calculation of the $K_i$ values for the inhibitors was performed by use of Activity Base. The $K_i$ value is calculated from $IC_{50}$ and the $K_m$ value is calculated using the Cheng Prushoff equation (with reversible inhibition that follows the Michaelis-Menten equation): $K_{i=IC50}(1+[S]/K_m)$ [Cheng, Y. C.; Prushoff, W. H. Biochem. Pharmacol. 1973, 22, 3099–3108]. The $IC_{50}$ is measured experimentally in an assay wherein the decrease of the turnover of cortisone to cortisol is dependent on the inhibition potential of each substance. The Ki values of the compounds of the present invention for the 11-β-HSD1 enzyme lie typically between about 10 nM and about 10 µM. Illustrative of the invention, the following Ki values have been determined in the human 11-β-HSD1 enzyme assay (see Table 1):

TABLE 1

Ki values determined in the human 11-β-HSD1 enzyme assay.

| Compound of Example | $K_i$ (nM) |
|---|---|
| 8 | 28 |
| 16 | 227 |

Compound Preparation

General:

For preparative straight phase HPLC purification a Phenomenex column (250×21.1 mm, 10 µm) was used on a Gilson system eluting with ethanol in chloroform (gradient from 0–10% in 10 min) with a flow of 20 mL/min. Column chromatography was performed on silica using Silica gel 60 (230–400 mesh), Merck. Melting points were determined on a Gallenkamp apparatus. Elemental analyses were recorded using a Vario EL instrument. HPLC analyses were performed using a Hypersil Elite column (150×4.6 mm, 3µ) with a flow of 3 mL/min on a Waters 600E system with monitoring at 254 nm Reverse phase preparative HPLC was carried out on a 100×21.2 mm, 5µ Hypersil Elite column eluting with a gradient of 5% ACN in 95% water to 95% ACN in 5% water (0.2% TFA buffer) over 10 mins at a flow rate of 20 mL/min with the UV detector set at 254 nm. Thin layer chromatography was carried out using pre-coated silica gel F-254 plates (thickness 0.25 mm). Electrospray MS spectra were obtained on a Micromass platform LCMS spectrometer. Cride, worked up compounds were purified by flash column chromatography using pre packed silica SPE columns (10 g silica) on an Isco Foxy 200 Combiflash system, and a gradient of 16.67% ethyl acetate in hexane increasing incrementally to 100% ethyl acetate.

List of Abbreviations

DCM=dichloromethane
DMAP=4-dimethylaminopyridine
DMF=dimethylfonmamide
DMSO=dimethyl sulfoxide
EDTA=ethylenediaminetetraacetic acid Sulfonamide Couplings:

Method A:

1 Eq of the 2-aminothiazole was dissolved in pyridine (0.5 M solution). The sulfonyl chloride (1.2 eq) was added and the reaction mixture was stirred at ambient temperature under nitrogen atmosphere for 15 h. The reaction mixture was poured into aqueous HCl (1 M). If the product precipitated it was collected on a filter and washed with aqueous HCl (1 M) and recrystalised from ethanol. In case an oil was obtained, the crude was extracted with DCM and worked up and purified using standard procedures.

Method B:

A solution of the 2-aminothiazole derivative (1 eq), triethylamine (2 eq) and DMAP (1 eq) in DMF (1 M) and DCM (0.225 ND was dispensed into a reaction vial. The sulfonyl chloride (1.2 eq) was dissolved in DCM (0.33 M) and added. The reaction mixtures were kept at room temperature over night. The mixture was then added to petroleum ether (10 times reaction volume). After some hours in refrigerator the supernatants were decanted and (a portion of) the residual materials were dissolved in DMSO-methanol-acetic acid (300 µL+500 µL+50 µL) and purified by preparative LCMS (acetonitrile-water gradients). The purest fractions were collected and lyophilized. Alternatively, the crude was isolated using extractive work-up and purified using standard procedures.

EXAMPLES

The following specific compounds were synthesized. The commercially available compounds thus only form embodiments, as indicated earlier in the description, as pharmaceutical compositions and use of said compounds as set out in the appended set of claims.

Example 1 [210P]

N-(5-Acetyl-4,5,6,7-tetrahydro[1,3]thiazolo[5,4c] pyridin-2-yl)-3-chloro-2-methylbenzenesulfonamide N-Acetyl4-piperidone (7.05 g, 0.05 mol) in acetic acid (35 mL) was treated dropwise with bromine (8.0 g, 0.05 mol) in acetic acid (10 mL) at room temperature. After 4 h, the formed precipitate was collected on a filter, washed with diethyl ether and air-dried. This crude intermediate (3.01 g) was dissolved in ethanol (20 mL) and after the addition of thiourea (0.76 g, 10.0 mmol)the reaction mixture was refixed for 4 h. The solvent was removed in vacuo. Water (20 mL) was added and the pH was adjusted to 9. Extraction with DCM, drying (sodium sulfate) and removal of the organic phase gave 1.1 g of a crude product. Modification by flash chromatography on silica gel gave 202 mg (10%) of 5-acetyl4,5,6,7-tetrahydro[1,3]thiazolo[5,4-c]pyridin-2-ylamine. This compound was sulfonylated with 3-chloro-2-methylbenzene sulfonyl chloride (234 mg, 1.02 mmol) in pyridine according to METHOD A. After workup, the final product was crystallised from methanol to afford 75 mg (%) of white crystals: $^1$H NMR (DMSO-$d_6$, 70° C.) δ 2.05 (s, 3H), 2.66 (s, 3H), 3.09 (m, 2H), 3.69 (m, 2H), 4.38 (m 2H), 7.37 (t, 1H), 7.64 (d, 1H), 7.91 (d, 1H), 12.53 (br s, NH).

Example 2 [211A]

2,4-dichloro-6methyl-N-(5,6,6-trimethyl-4,5,6,7-tetrahydro[1,3]thiazolo[5,4-c]pyridin-2-yl)benzenesulfonamide The title compound was prepared from 5,6,-tridmethyl4,5,6,7-tetrahydro[1,3]thiazolo[5,4-c]pyridin-2-amine (45 mg, 0.23 mmol) as described in the synthetic METHOD B to give a white solid (13.0 mg) with purity >90%. MS (pos) m/z 420.1, 422.1.

Example 3 [212A]

2,4-dichloro-6-methyl-N-[5-(4-morpholinylcarbonyl)-4,5,6,7-tetrahydro[1,3]thiazolo[5,4-c]pyridin-2-yl]benzenesulfonamide The title compound was prepared from 5-(4-morpholinylcarbonyl)4,5,6,7-tetrahydro[1,3]thiazolo[5,4-c]pyridin-2-amine (39 mg, 0.15 mmol) as described in the synthetic METHOD B to give a yellow solid (15.4 mg) with purity >90%. MS (pos) m/z491.1, 493.1.

Example 4 [234A]

2,4-Dichloro-6methyl-N-(4,5,6,7-tetrahydro-1,3-benzothiazol-2-yl)benzenesulfonamide The title compound was prepared from 4,5,6,7-tetrahydro-1,3-benzothiazol-2-amine as described in the synthetic METHOD B to give a white solid (10.8 mg) with purity >90%. MS (pos) m/z 377.1, 379.1.

Example 5 [234B]

4-Bromo-N-(5,6-dihydro-4H-cyclopenta[d][1,3]thiazol-2-yl2,5-difluorobenzenesulfonamide The title compound was prepared from 2-amino-5,6-dihydro4H-cyclopentathiazole hydrochloride (48 mg) and 4-bromo-2,5-difluorobenzenesulfonyl chloride (79 mg) as described in the synthetic METHOD B to give a yellow solid (2.5 mg) with purity >80%. MS (pos) m/z 395.2, 397.2; MS (neg) m/z 393.4, 395.4.

Example 6 [234C]

2,3,4-Trichloro-N-(5,6-dihydro-4H-cyclopenta[d][1,3]thiazol-2-yl)benzenesulfonamide The title compound was prepared from 2-amino-5,6-dihydro-4H-cyclopentathiazole hydrochloride (48 mg) and 2,3,4-tichlorobenzenesulfonyl chloride (76 mg) as described in the synthetic METHOD B to give a yellow solid (4.5 mg): MS (pos) m/z 383.3, 385.3, 387.3; MS (neg) m/z 381.4, 383.4, 385.4.

Example 7 [235A]

N-(2-{[(2,4-dichloro-6-methylphenyl)sulfonyl]amino}-4,5,6,7-tetrahydro-1,3-benzothiazol-6-yl)propanamide The title compound was prepared from N-(2-amino-4,5,6,7-tetrahydro-1,3-benzothiazol-6-yl)propanamide (47 mg, 0.21 mmol) and 2,4-dichloro-6-methylbenzenesulfonyl chloride as described in the synthetic METHOD B to give a white solid (20.3 mg) with purity >90%. MS (pos) m/z 448.1, 450.1.

Example 8 [236A]

2,4-Dichloro-N-(5,5-dimethyl-7-oxo-4,5,6,7-tetrahydro-1,3-benzothiazol-2-yl)-6- methylbenzenesulfonamide.

The title compound was prepared from 2-amino-5,5-dimethyl-5,6-dihydro-1,3-benzothiazol-7(4H)-one hydrobromide and 2,4-dichloro-6-methylbenzenesulfonyl chloride as described in the synthetic METHOD B to give a white-yellow solid (26 mg) with purity >90%: MS (pos) m/z 419.1, 421.1; HRMS m/z 417.9979 (calc. of monoisotopic mass for $C_{16}H_{16}Cl_2N_2O_3S_2$ gives 417.9979).

Example 9 [236B]

2,3,4-Trichloro-N-(5,5-dimethyl-7-oxo-4,5,6,7-tetrahydro-1,3-benzothiazol-2-yl)benzenesulfonamide The title compound was prepared from 2-amino-5,5-dimethyl-5,6-dihydro-1,3-benzothiazol-7(4H)-one (53 mg) and 2,3,4-trichlorobenzenesulfonyl chloride (76 mg) as described in the synthetic METHOD B to give a white solid (47.2 mg) with purity >90%: MS (pos) m/z 439.3, 441.3; HRMS m/z 437.9451 (calc. of monoisotopic mass for $C_{15}H_{13}Cl_3N_2O_3S_2$ gives 437.9433).

Example 10 [236C]

4,5-Dichloro-N-(5,4dimethyl-7-oxo-4,5,6,7-tetrahydro1,3-benzothiazol-2-yl)2-thiophenesulfonamide The title compound was prepared from 2-amino-5,5-dimethyl-5,6-dihydro-1,3-benzothiazol-7(4H)-one(53 mg) and 2,3-dichlorotiophene-5-sulfonyl chloride (68 mg) as described in the synthetic METHOD B to give a white-yellow solid (36.8 mg) with purity>90%: MS (pos)m/z411.3, 413.3.

Example 11 [236D]

4-Bromo-5-chloro-N-(5,5-dimethyl-7-oxo-4,5,6,7-tetrahydro-1,3-benzothiazol-2-yl)-2-thiophenesulfonamide The title compound was prepared from 2-amino-5,5-dimethyl-5,6-dihydro-1,3-benzothiazol-7(4H)one (53 mg) and 4-bromo-5-chlorothiophene-2-sulfonyl chloride (80 mg) as described in the synthetic METHOD B to give a white-yellow solid (47.1 mg) with purity >90%: MS (pos) m/z 455.2, 457.2.

Example 12 [236E]

3-Bromo-5chloro-N-(5,5-dimethyl-7-oxo-4,5,6,7-tetrahydro-1,3-benzothiazol-2-yl)2-thiophenesulfonamide The title compound was prepared from 2-amino-5,5-dimethyl-5,6-dihydro-1,3-benzothiazol-7(4H)-one (53 mg) and 3-bromo-5-chlorothiophene-2-sulfonyl chloride (80 mg) as described in the synthetic method to give a white solid (62.2 mg) with purity >90%: MS (pos) m/z 455.2, 457.2.

Example 13 [236F]

N-(5-Methyl-7-oxo-4,5,6,7-tetrahydro-1,3-benzothiazol-2-yl)-4-propylbenzenesulfonamide The title compound was prepared from 2-amino-5-methyl-5,6-dihydro-1,3-benzotliazol-7(4H)one (49 mg) and 4-n-propylbenzenesulfonyl chloride (59 mg) as described in the synthetic METHOD B to give a white solid (51.2 mg) with purity >90%: MS(neg) m/z 363.6; HRMS m/z 364.0911 (calc. of monoisotopic mass for $C_{17}H_{20}Cl_5N_2O_3S_2$ gives 364.0915).

Example 14 [236G]

4,5-Dichloro-N-(5-methyl-7-oxo-4,5,6,7-tetrahydro-1,3-benzothiazol-2-yl)-2-thiophenesulfonamide The title compound was 2-amino-5-methyl-5,6-dihydro-1,3-benzothiazol-7(4H)-one (49 mg) and 2,3-dichlorothiophene-5-sulfonyl chloride (68 mg) as described in the synthetic METHOD B to give a white solid (34.2 mg) with purity >90%: MS (pos) m/z 397.2, 399.2; MS (neg) m/z 395.2, 397.2.

Example 15 [236H]

2.4-Dichloro-6-methyl-N-(5-methyl-7-oxo-4,5,6,7-tetrahydro-1,3-benzothiazol-2-yl)benzenesulfonamide The title compound was 2-amino-5-methyl-5,6-dihydro-1,3-benzothiazol-7(4H)-one (49 mg) and 2,4-dichloro-6-methylbenzenesulfonyl chloride (70 mg) as described in the synthetic METHOD B to give a white solid (39.3 mg) with purity >90%: MS (pos) m/z 405.4, 407.4; MS (neg) m/z 403.4, 405.3.

Example 16 [236I]

4-Bromo-2methyl-N-(5methyl-7-oxo-4,5,6,7-tetrahydro-1,3-benzothiazol-2-yl)benzenesulfonamide The title compound was 2-amino-5-methyl-5,6-dihydro-1,3-benzothiazol-7(4H)-one (49 mg) and 4-bromo-2-methylbenzenesulfonyl chloride (73 mg) as described in the synthetic METHOD B to give a white solid (34.4 mg) with purity >90%: MS (pos) m/z 415.4, 417.4; MS (neg) m/z 413.4, 415.4.

Various embodiments of the present invention have been described above but a person skilled in the art realizes further minor alterations which would fall into the scope of the present invention. The breadth and scope of the present invention should not be limited by any of the above-described exemplary embodiments, but should be defined only in accordance with the following claims and their equivalents.

The invention claimed is:
1. A compound accordingly to the formula (I):

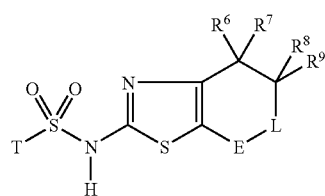

wherein
T is
I) thienyl, which optionally is substituted with at least one halogen or
II) phenyl substituted with
a) at least one of $C_{2-6}$ alkyl; or
b) at least one $C_{1-6}$ alkyl and at least one halogen; or
c) at least three halogens;
E is a bond, —CH$_2$— or —CO—;
L is a bond, —CH$_2$—, —CHR$^4$ — or —NR$^3$—;
R$^3$ is H, $C_{1-6}$ alkyl, $C_{1-6}$ acyl or —COR$^4$—;
R$^4$ is morpholinyl or $C_{1-6}$ amido;
R$^6$ and R$^7$ are independently hydrogen or $C_{1-6}$ alkyl and
R$^8$ and R$^9$ are independently hydrogen or $C_{1-6}$ alkyl, as well as pharmaceutically acceptable salts, hydrates and solvates thereof.

2. A compound according to claim 1, wherein
T is
I) thienyl, which is substituted with at least one halogen selected from chloro and bromo, or
II) phenyl substituted with
a) at least one n-propyl; or
b) at least one methyl and at least one halogen selected from chloro and bromo; or
c) at least three halogens selected from fluoro, bromo and chloro;
E is a bond, —CH$_2$— or —CO—;
L is a bond, —CH$_2$—, —CHR$^4$— or —NR$^3$—;
R$^3$ is methyl, acetyl or —COR$^4$;
R$^4$ is morpholinyl or propionamido;
R6 and R$^7$ are both hydrogen; and
R$^8$ and R$^9$ are independently hydrogen or methyl.

3. A compound according to claim 1, selected from the group of:
N-(5-Acetyl-4,5,6,7-tetrahydro[1,3]thiazolo[5,4-c]pyridine-2-yl)3-chloro-2 methylbenzenesulfonamide;
2,4-dichloro-6-methyl-N-(5,6,6-trimethyl-tetrahydro[1,3]thiazolo[5,4-c]pyridine-2-yl)benzenesulfonamide;
2,4-dichloro-6-methyl-N-[5-(4-morpholinylcarbonyl)-4,5,6,7-tetrahydro[1,3]thiazolo[5,4-c]pyridin-2-yl]benzenesulfonamide;
2,4,-dichloro-6-methyl-N-(4,5,6,7-tetrahydro-1,3-benzothiazol-2-yl)benzenesulfonamide;
4-bromo-N-(5,6-dihydro-4H-cyclopenta[d][1,3 ]thiazol-2-yl)-2,5-difluorobenzenesulfonamide;
2,3,4-trichloro-N-(5,6-dihydro-4H-cyclopenta[d][1,3]thiazol-2-yl)benzenesulfonamide;
N-(2-{[(2,4-dichloro-6-methylphenyl)sulfonyl]amino}-4,5,6,7-tetrahydro-1,3-benzothiazol-6-yl)propanamide;
2,4-dichloro-N-(5,5-dimethyl-7-oxo-4,5,6,7-tetrahydro-1,3-benzothiazol-2-yl)-6-methylbenzenesulfonamide;
2,3,4-Trichloro-N-(5,5-dimethy-7-oxo-4,5,6,7-tetrahydro-1,3-benzothiazol-2-yl)benzenesulfonamide;
4,5-dichloro-N-(5,5,-dimethyl-7-oxo-4,5,6,7-tetrahydro-1,3-benzothiazol-2-yl)-2-thiophenesulfonamide;
4-bromo-5-chloro-N-(5,5-dimethyl-7-oxo-4,5,6,7-tetrahydro-1,3-benzothiazol-2-yl)-2-thiophenesulfonamide;
3-bromo-5-chloro-N-(5,5-dimethyl-7-oxo-4,5,65,7-tetrahydro-1,3-benzothiazol-2-yl)-2-thiophenesulfonamide;
N-(5-Methyl-7-oxo-4,5,6,7-tetrahydro-1,3-benzothiazol-2-yl)-4-propylbenzenesulfonamide;
4,5-dichloro-N-(5-methyl-7-oxo-4,5,6,7-tetrahydro-1,3-benzothiazol-2-yl)-2-thiophenesulfonamide;
2,4-dichloro-6-methyl-N-(5-methyl-7-oxo-4,5,6,7-tetrahydro-1,3-benzothiazol-2-yl)benzenesulfonamide and
4-bromo-2-methyl-N-(5-methyl-7-oxo-4,5,6,7-tetrahydro-1,3-benzothiazol-2-yl)benzenesulfonamide.

4. A process for the preparation of a compound according to claim 1 comprising at least one of the following steps:
a) sulfonamide coupling by reacting a 2-aminothiazole with a sulfonylchloride in the presence of a base,
b) sulfonamide coupling by reacting a 2-aminothiazole derivative with a sulfonyichloride in the presence of a base.

5. A method for the treatment of diabetes, syndrome X, obesity, glaucoma, hyperlipidemia, hyperglycemia or hyperinsulinemia, said method comprising administering to mammal, in need of such treatment, an effective amount of a compound having the formula (I):

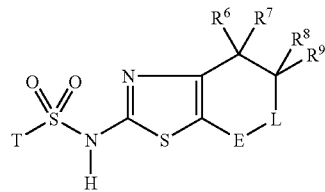

wherein

T is
I) thienyl, which optionally is substituted with at least one halogen or
II) phenyl substituted with
a) at least one of $C_{2-6}$ alkyl; or
b) at least one $C_{1-6}$ alkyl and at least one halogen; or
c) at least three halogens;

E is a bond, —$CH_2$— or 13 CO—;
L is a bond, —$CH_2$—, —$CHR^4$— or $NR^3$—;
$R^3$ is H, $C_{1-6}$ alkyl, $C_{1-6}$ acyl or $COR^4$—;
$R^4$ is morpholinyl or $C_{1-6}$ amido;
$R^6$ and $R^7$ are independently hydrogen or $C_{1-6}$ alkyl and
$R^8$ and $R^9$ are independently hydrogen or $C_{1-6}$ alkyl, as well as pharmaceutically acceptable salts, hydrates and solvates thereof.

6. A method according to claim 5, wherein
T is
I) thienyl, which optionally is substituted with at least one halogen selected from chloro and bromo, or
II) phenyl substituted with
a) at least one n-propyl; or
b) at least one methyl and at least one halogen selected from chloro and bromo; or
c) at least three halogens selected from fluoro, bromo and chloro;

E is a bond, —$CH_2$— or —CO—;
L is a bond, —$CH_2$—, —$CHR^4$— or —NR—
$R^3$ is methyl, acetyl or —$COR^4$;
$R^4$ is morpholinyl or propionamido;
$R^6$ and $R^7$ are both hydrogen; and
$R^8$ and $R^9$ are independently hydrogen or methyl.

7. A method according to claim 5, wherein the compound is selected from the group of:
N-(5-Acetyl-4,5,6,7-tetrahydro[1,3]thiazolo[5,4-c]pyridine-2-yl)3-chloro-2methylbenzenesulfonamide;
2,4-dichloro-6-methyl-N-(5,6,6-trimethyl-tetrahydro[1,3]thiazolo[5,4-c]pyridine-2-yl)benzenesulfonamide;
2,4-dichloro-6-methyl-N-[5-(4-morpholinylcarbonyl)-4,5,6,7-tetrahydro[1,3]thiazolo[5,4-c]pyridin-2-yl]benzenesulfonamide;
2,4,-dichloro-6-methyl-N-(4,5,6,7-tetrahydro-1,3-benzothiazol-2-yl)benzenesulfonamide;
4-bromo-N-(5,6-dihydro-4H-cyclopenta[d][1,3 ]thiazol-2-yl)-2,5-difluorobenzenesulfonamide;
2,3,4-trichloro-N-(5,6-dihydro-4H-cyclopenta[d][1,3 ]thiazol-2-yl)benzenesulfonamide;
N-(2-{[(2,4-dichloro-6-methylphenyl)sulfonyl]amino}-4,5,6,7-tetrahydro-1,3-benzothiazol-6-yl)propanamide;
2,4-dichloro-N-(5,5-dimethyl-7-oxo-4,5,6,7-tetrahydro-1,3-benzothiazol-2-yl)-6-methylbenzenesulfonamide;
2,3,4-Trichloro-N-(5,5-dimethy-7-oxo-4,5,6,7-tetrahydro-1,3-benzothiazol-2-yl)benzenesulfonamide;
4,5-dichloro-N-(5,5,-dimethyl-7-oxo-4,5,6,7-tetrahydro-1,3-benzothiazol-2-yl)-2-thiophenesulfonamide;
4-bromo-5-chloro-N-(5,5-dimethyl-7-oxo-4,5,6,7-tetrahydro-1,3-benzothiazol-2-yl)-2-thiophenesulfonamide;
3-bromo-5-chloro-N-(5,5-dimethyl-7-oxo-4,5,65,7-tetrahydro-1,3-benzothiazol-2-yl)-2-thiophenesulfonamide;
N-(5-Methyl-7-oxo-4,5,6,7-tetrahydro-1,3-benzothiazol-2-yl)-4-propylbenzenesulfonamide;
4,5-dichloro-N-(5-methyl-7-oxo-4,5,6,7-tetrahydro-1,3-benzothiazol-2-yl)-2-thiophenesulfonamide;
2,4-dichloro-6-methyl-N-(5-methyl-7-oxo-4,5,6,7-tetrahydro-1,3-benzothiazol-2-yl)benzenesulfonamide and p1 4-bromo-2-methyl-N-(5-methyl-7-oxo-4,5,6,7-tetrahydro-1,3-benzothiazol-2-yl)benzenesulfonamide.

8. A pharmaceutical composition comprising at least one compound according to claim 1, and a pharmaceutically acceptable carrier.

* * * * *